United States Patent [19]
Holm

[11] Patent Number: 5,881,954
[45] Date of Patent: *Mar. 16, 1999

[54] METHOD AND DEVICE FOR ATOMISING FLUIDS

[75] Inventor: Steen Erik Holm, Viborg, Denmark

[73] Assignee: Danmist APS, Aalbor, Denmark

[*] Notice: This patent issued on a continued prosecution application filed under 37 CFR 1.53(d), and is subject to the twenty year patent term provisions of 35 U.S.C. 154(a)(2).

[21] Appl. No.: 537,931

[22] PCT Filed: Apr. 28, 1994

[86] PCT No.: PCT/DK94/00172

§ 371 Date: Dec. 20, 1995

§ 102(e) Date: Dec. 20, 1995

[87] PCT Pub. No.: WO94/25176

PCT Pub. Date: Nov. 10, 1994

[30] Foreign Application Priority Data

Apr. 30, 1993 [DK] Denmark .................................. 0489/93

[51] Int. Cl.⁶ .................................................. B05B 17/04
[52] U.S. Cl. ................................ 239/4; 239/99; 239/456; 239/515
[58] Field of Search ........................ 239/4, 102.1, 102.2, 239/456, 459, 505, 506, 513, 514, 515, 541, 99, 453, 516, 533.1; 128/200.14, 200.18, 200.22, 200.23

[56] References Cited

U.S. PATENT DOCUMENTS

| 3,693,656 | 9/1972 | Sauer .............................. 239/533.1 X |
| 4,049,200 | 9/1977 | Sobol . |
| 4,165,038 | 8/1979 | Kumazawa ......................... 239/516 X |
| 4,221,331 | 9/1980 | Goran, Jr. . |
| 5,056,511 | 10/1991 | Ronge . |

FOREIGN PATENT DOCUMENTS

| 0 387 179 A2 | 9/1990 | European Pat. Off. . |
| 0 520 571 A1 | 12/1992 | European Pat. Off. . |
| 954901 | 1/1950 | France . |
| 726916 | 3/1955 | France . |
| 5704354 | 7/1987 | WIPO . |
| WO 91/14468 | 10/1991 | WIPO . |
| WO 92/19383 | 11/1992 | WIPO . |

*Primary Examiner*—Andres Kashnikow
*Assistant Examiner*—Steven J. Ganey
*Attorney, Agent, or Firm*—Merchant, Gould, Smith, Edell, Welter & Schmidt

[57] ABSTRACT

By a method of atomising fluids a predetermined amount of fluid is provided between a first surface (63) and a second surface (68) being spaced from one another. The two surfaces (63, 68) are then moved towards one another, until the first surface over its entire extent essentially is in contact with the second surface. The movement is carried out at such a speed that the fluid between the two surfaces is pressed out to the ambience via the periphery of the surfaces with a velocity sufficient to atomise the fluid.

10 Claims, 4 Drawing Sheets

METHOD AND DEVICE FOR ATOMISING
FLUIDS

TECHNICAL FIELD

The invention relates to a method of atomising fluids and a device for carrying out said method.

BACKGROUND ART

Several devices and nozzles for a fine atomization of fluids or suspensions are known from the patent literature.

From WO 91/14468 it is known to produce a spray of droplets by forcing a fluid through a small opening under high pressure.

Further, EP-A1-0 520 571 discloses an atomising nozzle for providing a spray of droplets comprising an orifice having a closure member movable between a position, in which it closes the orifice and a position spaced herefrom to define a gap. Under the action of pressurised fluid, the closure member is displaced relative to the orifice to define the gap, whereby a fluid film flows through the gap and breaks into droplets.

Moreover, from WO 92/19383 it is known to atomise a stream of fluids into droplets by said stream impinging a body placed in the discharge path at great velocity.

Finally EP-A2-0 387 179 discloses an atomising device, in which pressurised fluid is discharged through a vibrating-type atomising nozzle comprising a seat part having an outlet opening and a closing element biased towards a closed position by means of a spring, in which it closes the outlet opening. By means of an electromechanical drive means the closing element may be oscillated between a closed and opened position relative to the seat part, whereby the pressurised fluid will be discharged from the outlet opening, when the closing element is in its open position.

Within the pharmaceutical field it is known to administer a medicament in solution or suspension as a fine spray through the nose or mouth. For inhalation purposes, the droplets of the spray have to be so small, i.e. about 10 micrometer or less, that they may be extrained by the inhaled air and reach their destination, i.e. the outer most alveoli in the lungs.

In order to obtain sufficiently small droplets, it has been the practice for many years to atomise the medicament in solution or suspension by means of a propellant usually of the freon-type. For environmental reasons and due to the physiological effect it is desirable to avoid the use of more or less inert propellants.

DISCLOSURE OF THE INVENTION

The object of the invention is to provide a method and a device for fine atomization of fluids, in particular medicaments in solution or suspension, in a vehicle, such as water, by means of which it is possible to form a spray of fluid with a droplet size of about 10 $\mu$ or less.

According to the invention, the method for atomising fluid is characterised in that a predetermined quantity of fluid is provided between a first surface and a second surface spaced from one another, whereafter the two surfaces are moved towards one another, until the first surface essentially over its entire extent essentially is in contact with the second surface and at such a speed that the fluid between the two surfaces is pressed out to the ambience via the periphery of the surfaces with a velocity sufficient to atomise the fluid.

The invention is thus based on the knowledge that a very fine atomization of a fluid can be obtained, if two surfaces, between which a certain dosage of fluid is present, are moved towards one another at sufficient speed for a thin fluid film to be sprayed out at the edge of the surfaces. The fluid film subsequently becomes instable and separates into fluid strings, which are broken up into droplets of a diameter less than the initial thickness of the fluid film under the influence of the surface tension of the fluid. Compared to known principles of atomization without the use of propellants, by the present invention it is thus avoided to pressurised large quantities of fluids, as essentially only the limited quantity of fluid placed between the surfaces, is pressurised. This is particularly advantageous when carrying out the invention by means of a small hand-held device for the administration of a drug, i.e. a so-called inhalator.

According to the invention, the two surfaces may have essentially complementary shapes. This embodiment of the invention is at present the most preferred.

Moreover, according to the invention, the fluid may be supplied through an outlet which opens into one of the surfaces, preferably centrally therein.

Finally, according to the invention, the two surfaces alternately may be moved between the position, in which they are spaced from one another and the position, in which they essentially are in contact with one another, preferably with a frequency of 10 to 100 Hz. In this embodiment of the invention an essentially continuous fine atomization of fluid is obtained during the alternate movement. In connection with an inhalator the time interval may be 2 seconds.

The term essential contact between the two surfaces is used herein to denote that the two surfaces not necessarily are brought into direct surface engagement, but that they may be slightly spaced apart, viz. corresponding to half, a third or less of the initial fluid film thickness between the surfaces. At a typical film thicknesss of about 20 $\mu$, the surfaces thus may be brought into an end position, in which they are interspaced by e.g. 5 $\mu$ or less and the intended atomising effect may still be obtained. This is particularly essential when a suspension is to be atomised, where the surfaces should not be brought closer together than the particle size of the suspension, as the particles otherwise will be compressed and possibly adhere to one of the surfaces. At atomization of solutions the surfaces may naturally be brought into direct engagement with one another.

The device according to the invention for carrying out the method according to the invention is characterised in that it comprises a first pressing means having a first surface and a second pressing means having a second surface, said pressing means being arranged with the surfaces facing one another, a drive means for moving one of the pressing means alternately between a position, in which the surfaces of the pressing means are spaced from one another and a position, in which said surfaces essentially engage one another over their entire extent; a fluid outlet opening into an area between the two pressing means, said outlet comnmunicating with a fluid supply and a dosage means through a fluid supply passage, said dosage means supplying a predetermined quantity of fluid to the area between the two pressing means through the fluid outlet, when said means are spaced from one another.

Consequently, as previously described in relation to the method according to the invention, the quantity of fluid placed between the pressing means is pressed out as a thin fluid film breaking into fine droplets, when the surfaces of the two pressing means are moved towards one another.

According to the invention, the device may comprise a stationary and a movable pressing means. This embodiment of the invention is at present the most preferred.

Furthermore, according to the invention, the drive means may be an electromagnetic drive means comprising a displacable magnetic or electricly conducting core for acting on the movable pressing means and a fixedly arranged coil circumscribing the core, an annular gap being formed therebetween, said coil being supplied intermittently with power from a power supply. The drive means may also be of a purely mechnical or piezo-electric type.

The core may act intermittently on the movable pressing means to urge the surface thereof into contact with the surface of the second pressing means. The movable pressing means returns to the position, in which its surface is spaced from the surface of the second pressing means by means of a return member, e.g a spring biassing the movable pressing means to the said position. Alternatively, a biassing means, such as a spring, may provide the pressing movement and the core may provide the return movement by supplying power to the coil.

In connection with the above embodiment of the invention, the core may be fixedly connected to the movable pressing means. As a result, the polarity of the the power supplied may be reversed alternately, whereby by means of the power supplied the movable pressing means is moved into a position, in which the surfaces of the two pressing means are in contact with one another as well as into a position in which said surfaces are spaced from one another. In addition hereto the movable means may also be moved to the contact position by means of a biassing means, such as a spring, as mentioned above.

Moreover, according to the invention, the surfaces of the two pressing means may have essentially complementary shapes, such as being essentially planar. Other surface shapes may, however, also be used, such as conical or spherical.

Furthermore, according to the invention, one of the surfaces of the pressing means may be slightly concave for the formation of a projecting circumferential edge and formed of a resilient material. When moving the two pressing means towards one another, the surfaces thereof initially form a closed compartment containing the quantity of fluid. At the continuous movement of the pressing means, the fluid is pressurised and pressed out via the circumferential edge which is deformed simultaneously.

Moreover, in connection with the above embodiment of the invention the projecting circumferential edge may essentially abut the surface of the second pressing means in the position, in which the surfaces are spaced from one another. Consequently, it is ensured that the dosed fluid quantity is reliably retained between the two surfaces, until these are moved towards one another.

Finally, according to the invention stop means may be associated with the pressing means for determining a minimum spacing between the two surfaces. In this connection the stop means is formed by at least one projection extending from the surface of one of the pressing means and is intended to abut the surface of the other pressing means. The provision of a stop means is particularly advantageous at atomization of suspensions, as the stop means prevents the surfaces of the pressing means from direct engagement with one another and thereby the particles in the suspension from being compressed. When the drive means is a magnetic or electricly conductive core circumscribed by an electric coil, the stop means may comprise an electrical control system accurately determining the engagement position of the pressing means.

BRIEF DESCRIPTION OF THE DRAWINGS

The invention is described in greater detail in the following with reference to the accompanying drawings, in which.

BEST MODE FOR CARRYING OUT THE INVENTION

Figure 1:
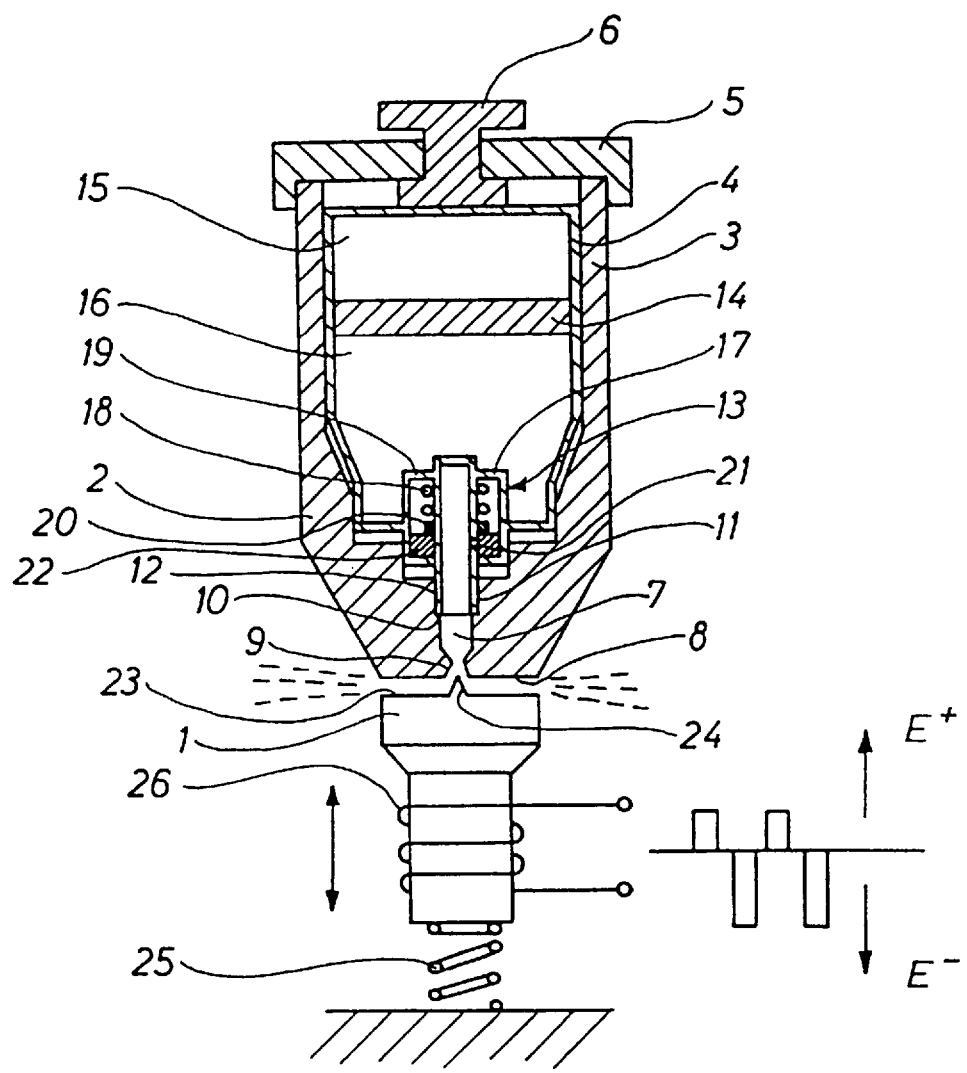
FIG. 1 is a diagrammatic axial sectional view through a first embodiment of a device according to the invention.

The atomising device according to the invention shown in FIG. 1 comprises a first pressing means 1 formed of a movable pressing part and a second pressing means 2 arranged co-axially therewith and means formed as a stationary pressing part.

At its upper end, the stationary pressing part 2 is provided with a compartment 3, in which a small medicine container 4 is placed. The compartment is closed by means of a cover 5. The compartment 3 is shaped complementary to the small medicine container 4 being axially movable arranged in the compartment. The small medicine container 4 is moved by means of an activation button 6 extending through the cover 5.

Furthermore, the stationary part 2 has an axial outlet passage 7 opening into a lower pressing surface 8 via an outlet opening 9. The outlet opening 9 passes via a ledge 10 into an enlarged bore 11 intended to receive a discharge tube 12 of a discharge valve 13 of a known type arranged on the mouth of the small medicine container.

By means of a piston 14 the small medicine container 4 is divided into an upper pressure chamber 15 containing a pressure medium, and a lower supply chamber 16 containing the fluid medicament in solution or suspension to be dispensed. The discharge tube 12 of the discharge valve 13 is displaceably arranged in a housing 17 being continuously supplied with fluid from the supply chamber 16. By means of a spring 18 arranged between an end wall 19 of the housing 17 and on a shoulder 20 of the discharge tube 12, said latter tube is biassed towards the closed position shown in FIG. 1. In the closed position, a radial hole 21 in the discharge tube is sealed by means of a seal 22 being fixedly attached to the valve housing 17. When the discharge tube is displaced in an inwardly direction, the radial hole 21 is brought out of sealing engagement with the seal and forms a fluid communication between the supply chamber 16 and interior of the discharge tube 12, whereby fluid flows out through the tube. The fluid communication and the outflow of fluid are obtained by pressing the activation button 6 and thereby the small container, except the discharge tube 12.

The lower movable pressing part 1 has a plane upper pressing surface 23 arranged opposite the pressing surface 8 of the stationary pressing part 2. A conical nose 24 extends centrally from the pressing means 23. The nose 24 is intended to coact with the outlet opening 9 of the stationary part. By means of a spring 25, the movable part 1 is biassed towards the stationary part 2 to a position, in which the two pressing surfaces 8,23 of the parts abut one another. An electric coil 26 is arranged about a portion of the movable part 1 containing a magnetic or electrically conductive material, said coil 26 being intermittently supplied with negative and positive pulses from a power supply. The positive pulses cause the movable pressing part 1 to move towards the stationary pressing part 2, said movement being assisted by the force from the spring 18, while the negative pulses cause the movable pressing part 1 to move away from the stationary pressing part 2 against the spring force. Alternatively, only negative pulses may be supplied intermittently, whereby the force from the spring 18 causes the movable pressing part 1 to move towards the stationary pressing part 2.

The device operates in the following manner:

In the initial position, the pressing surfaces of the two pressing parts abut one another and the outlet opening 9 of the stationary pressing part being closed as the conical nose 24 of the movable pressing part is in sealing engagement therewith. When pressing the activation button 6, the small medicine container 4 is displaced relative to its discharge tube 12, whereby the pressurised fluid flows into the compartment defined by the interior of the discharge tube 12 and the outlet passage 7. When the power supply is switched on, the movable pressing part 1 is moved intermitenly away from and towards the stationary pressing part 2. During movement of the movable part 1 away from the stationary part, a small amount of fluid flows out of outlet opening 9 of the stationary part and down onto the pressing surface 23 of the movable part 1. When the movable part is moved towards the stationary part, the amount of fluid between the pressing surfaces of the parts is compressed therebetween and pressed out to the ambience via the periphery of the pressing surfaces. The fluid film is instable and forms fluid strings which are subsequently broken up into fine droplets.

During a subsequent downwards movement of the movable pressing part 1, a small amount of fluid is once more discharged onto the pressing surface 23 thereof. As described above, the amount of fluid is pressed out to the ambience as a thin film, when the movable part 1 subsequently is moved into contact with the stationary pressing part. When the button 6 is released and the power to the coil 26 is switched off, the discharge of fluid is stopped and the movable part is is brought into abutment with the stationary part.

Experience has shown that the fluid film has to have a velocity of 5 to 10 m/s to break into fine droplets. Calculations have shown that, if a fluid film thickness of 20 micrometer is placed on a pressing surface of a diameter of 8 mm, the fluid film obtains a velocity of about 10 m/s, provided the pressing surfaces are moved towards one another at a speed of about 0.1 mls. The discharged amount of fluid is about 1 microlitre per stroke, i.e. for discharging a total amount of fluid of 50 microlitre, which is usually the amount of fluid discharged by medical inhalators, 50 strokes are required. Consequently, if the discharge is to be provided within two seconds, the stroke frequency is to be 25 Hz.

Figure 2:
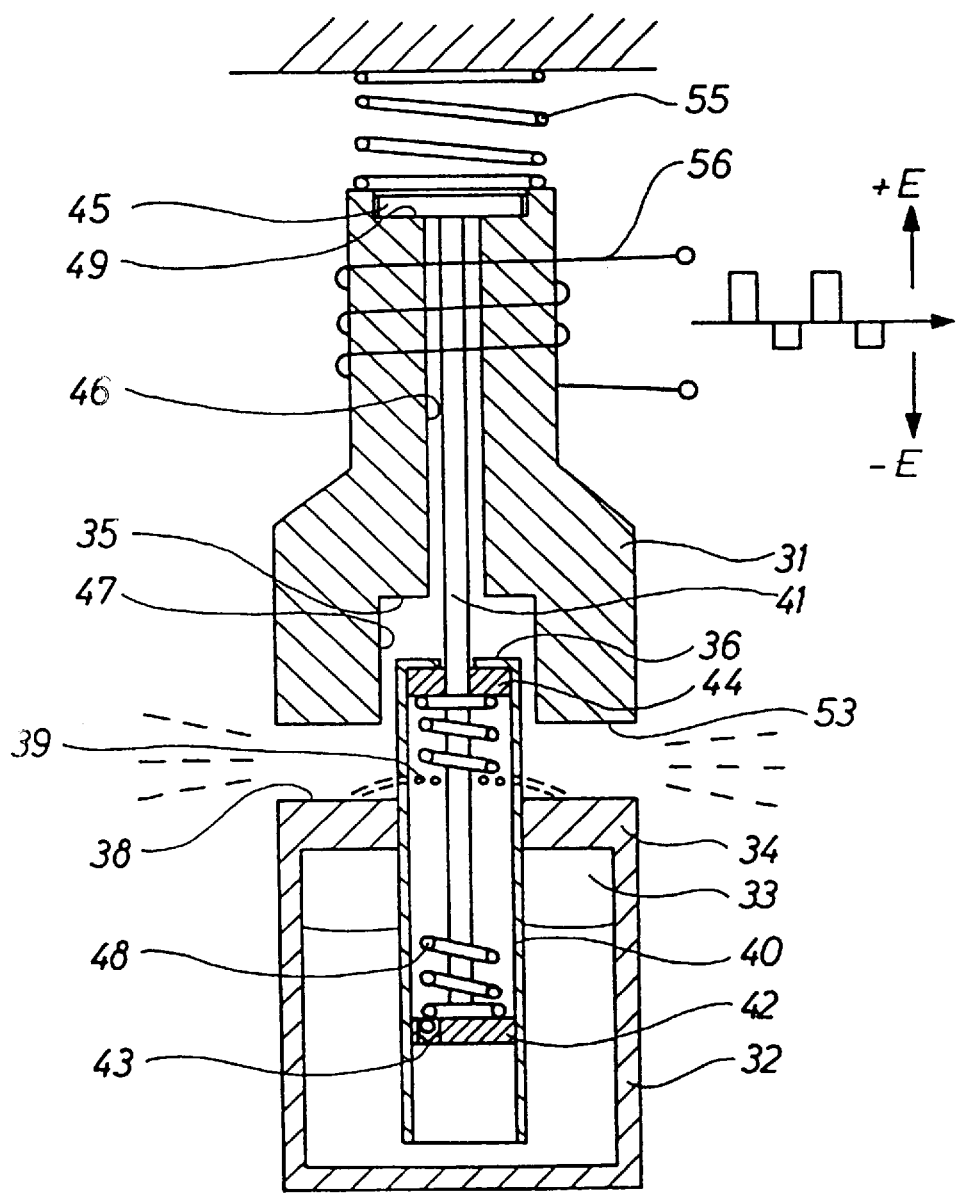
FIG. 2 is a diagrammatic axial sectional view through a second embodiment of a device according to the invention.

The embodiment of the atomising device according to the invention shown in FIG. 2 comprises a movable pressing part 31 and a stationary pressing part 32. The stationary part 32, shown on the drawing as the lower part has a cavity forming a supply chamber 33 for the fluid to be discharged. The fluid may be supplied to the chamber via a sealable opening (not shown). The stationary part 32 has an upper wall 34, whose upper surface forms a pressing surface 38. A cylinder 40 extends centrally through the upper wall 34 and has a lower open end being submerged in the fluid in the chamber 33 and an upper end extending beyond pressing surface 38. Immediately above the pressing surface, a plurality of outlets 39 are provided in the cylinder. The cylinder 40 has an end wall 36, through which a piston rod 41 extends, said rod being sealed by means of a seal 44. At its lower end, the piston rod 41 is provided with a piston 42 being in sealing engagement with the inner face of the cylinder. The piston 42 is provided with a one-way valve 43 allowing the fluid to flow from the lower face to the upper face of the piston 42, and preventing the fluid from flowing in the opposite direction. At its upper end, the piston rod 41 is provided with a flange 45 abutting an end face 49 of the movable part 31 in the position shown. Furthermore, a compression spring 48 is arranged about the piston rod 41, said spring being compressed between the upper face of the piston and the lower face of the sealing 44 and intended to bring the flange 45 into engagement with the end face 49.

The movable pressing part 31 has a first small axial bore 46 receiving the piston rod 41 and passsing into a large axial bore 47 via a ledge 35, the projecting portion of the cylinder 40 being received in said large bore 47. At its lower end, the movable part 31 is provided with a plane pressing surface 53. By means of a compression spring 55, the movable part 31 is biassed towards a position in which the ledge 35 abuts the upper face of the end wall 36 of the cylinder 40. In this position (the pressing position), the pressing surface 53 of the movable part 31 is spaced from the pressing face 38 of the stationary part 32 by a few micrometers.

Finally, an electric coil 56 is arranged about a portion of the movable part 31 being magnetically or electrically conductive. The electric coil 56 may be supplied intermittently with positive and negative pulses from a power supply. When supplying a positive pulse, the coil 56 pulls the movable part upwards against the force from the spring 55 to the position shown in the Figure. When supplying a negative pulse, assisted by the force from the spring 55, the movable part 31 is moved downwards, until its ledge 35 abuts the end wall 36 of the cylinder 40 and the pressing face 53 is spaced slightly apart from the pressing face 38 of the lower stationary part 32.

The apparatus shown in FIG. 2 operates in the following manner:

By supplying a positive pulse to the coil 56, the movable part 31 is moved upwards, whereby also the piston 42 attached to the lower end of the piston rod 41 is moved upwards. Consequently, an amount of fluid is discharged onto the pressing face 38 of the lower part 32 via the outlet openings 39 in the cylinder wall. By supplying a negative pulse to the coil 56 or alternatively by merely disconnecting the positive pulse, the movable part 31 is moved downwards due to the bias from the spring 55, whereby the discharged amount of fluid is compressed between the pressing faces 53, 38 and pressed out to the ambience via the periphery as a thin fluid film breaking into droplets in the manner described above. As the ledge 35 abuts the end wall 36 of the cylinder 40, the two pressing faces 38, 53 do not come into direct contact with one another, which is advantageous at the discharge of suspensions, as it is thereby prevented that the particles of the suspension are compressed and adhere to the pressing faces. During the pressing stroke and the subsequent period between the pulses, the spring 48 brings the flange, 48 into abutment with the ledge 49, whereby fluid flows through the one-way valve 43.

Figure 3:
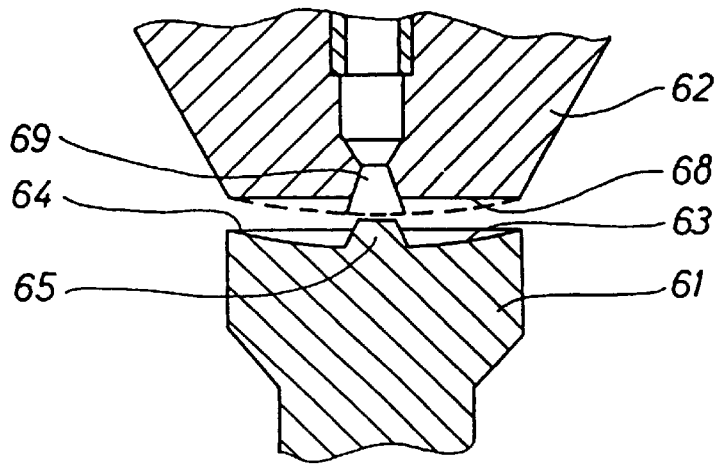
FIG. 3 is an axial sectional view through the coacting areas of the alternatively formed pressing means of a device according to the invention.

Relative to the embodiment shown in FIG. 1, FIG. 3 shows an alternative embodiment of the pressing faces of the part. In this embodiment, the upper pressing part 62 has a plane pressing face 68, while the lower pressing part 61 has a slightly concave pressing face 63 ending in a circumferential edge 64 and being formed of a resilient material.

When the two parts are moved into contact with one another, the pressing face 63 of the lower part 61 is deformed due to its resilience and the amount of fluid is initially enclosed in a compartment formed by the engagement of the circumferential edge 64 with the pressing face 68 of the upper part 62. By continuously moving the two pressing faces towards one another, the pressing face 63 of the lower part 61 is deformed and the fluid is pressed out to the ambience as a film by deformation of the edge portion of the lower part 61. During the compression the conical nose 65 protruding from the pressing face 63 of the lower part 61 closes the outlet opening 69 in the upper part 62.

As indicated by dotted lines in FIG. 3, the upper pressing part 62 may have a convex pressing face having a form essentially complementary to the pressing face 63 of the lower pressing part 62. In this embodiment, the pressing face 63 of the lower part 61 may also be formed of a non-deformable material.

Figure 4:
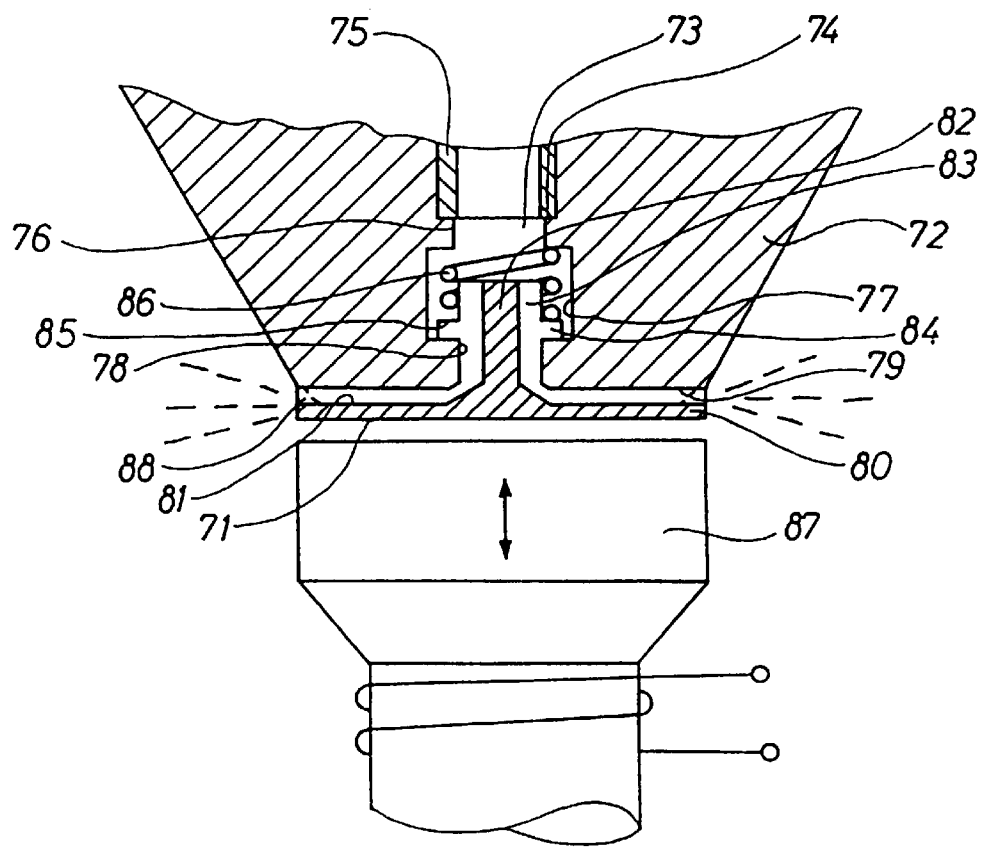
FIG. 4 is an axial sectional view through the coacting areas of the alternatively formed pressing means of a device according to the invention.

Relative to the embodiment of FIG. 1, FIG. 4 shows a further alternative embodiment of the pressing means. Apart from the modifications shown in the Figure (described in details below), the upper pressing means is formed corresponding to the stationary pressing means described above with reference to FIG. 1. Starting at the ledge 74 forming a rest for the discharge tube 75 of the small medicine container, the outlet passage 73 of the stationary pressing means 72 is provided with a first portion 76, a chamber-like portion 77 subjacent thereto of a larger diameter and an portion 78 subjacent thereto being of a smaller diameter than the chamber-like portion and opening into the pressing face 79 of the stationary pressing means 72.

The movable pressing means 71 is provided with a plate-shaped element 80 with an upwards facing pressing surface 81 arranged opposite the pressing face 79 of the stationary pressing means 72. A central stem 82 extends centrally upwards from the pressing face 81 and is provided with a plurality of radial ribs 83, each being provided with a radially outwardly projection 84. The central stem extends through the portion 78 of the small diameter and into the chamber-like portion 77 of the stationary pressing means 72. The outer periphery of the radial ribs engages the inner surface of the portion 78 of a small diameter in order to guide the movable pressing means 71 in relation to the stationary pressing means 72. The projections 84 of the radial ribs 83 are arranged in the chamber-like portion 77 and by means of a spring 86 forced towards a ledge 85 between the chamberlike portion 77 and the portion 78 of a small diameter. In the position shown on the Figure, the pressing face 81 of the movable pressing means 71 is spaced apart from the pressing face 79 of the stationary pressing means 72 to form a gap for receiving an amount of fluid discharged from the small medicine container via the outlet passage 73. Due to its low height, typically being in the order of 20 micrometer or less, the gap has an retaining effect on the discharged fluid which adheres to the pressing faces 79,81. In order to further ensure that the amount of fluid is retained, the pressing face 81 of the movable pressing means 71 may be provided with a projecting circumferential edge 88 (indicated by dotted lines), formed of a resilient material. The circumferential edge 88 ensures that the amount of fluid discharged between the pressing faces 71,81 is retained and may abut the pressing face 79 of the stationary pressing means 72, when the pressing faces are spaced apart from one another to make completely sure that the amount of fluid is retained, until the pressing faces are moved towards one another. By moving the pressing faces towards one another, the fluid is pressed out at deformation of the circumferential edge 88 of the movable pressing means 71.

A drive means 87 is arranged subjacent the movable pressing means 71, said drive means intended to act on the movable pressing means 71 to move the pressing face 81 thereof towards the pressing face 79 of the stationary means 72, thus pressing out an amount of fluid present between the pressing faces as a thin film breaking into droplets.

As indicated in the Figure, the drive means may be formed of a core with a magnetic or electricly conductive portion, about which an electric coil is arranged. By alternately supplying the coil with positive and negative pulses from a power supply, the core alternately acts on the movable pressing means 71. Due to the force from the spring 86, the movable pressing means 71 returns to the initial position shown in the Figure, when it is not acted upon by the drive means 87. In the arrangement shown, the core of the drive means 87 has such a speed, when it acts on the movable pressing means 71 that a high acceleration of the movement of the movable pressing means 71 is achieved, which is particularly advantageous for quickly obtaining a high velocity of the fluid pressurization and thus of the fluid film pressed out.

Figure 5:
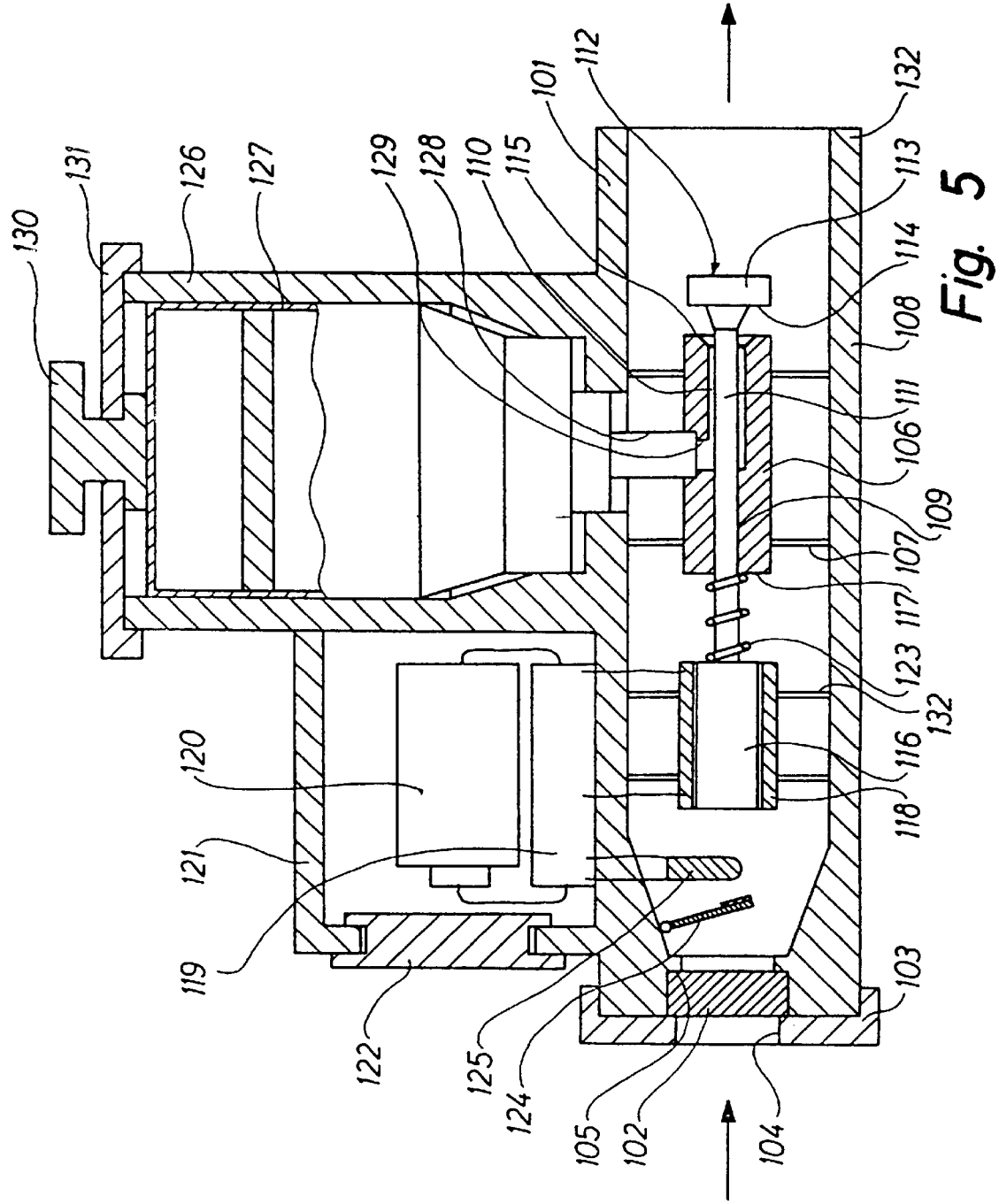
FIG. 5 shows a third embodiment of the device according to the invention formed as an inhalator.

FIG. 5 illustrates an embodiment of the atomization device according to the invention formed as an inhalator for inhalation of a fluid medicine. The device comprises a hollow, cylindrical inhalation part 101, a filter 102 being provided at one end thereof, said filter being fixed between a cover 103 with an opening 104 and a ledge 105. In the interior of the inhalation part 101, a stationary pressing part 106 is arranged coaxially and connected to the wall 108 of the inhalation part by means of connecting rods 107.

The stationary pressing part 106 is provided with an axial bore comprising a guide portion 109 and a passage 110 of a diameter larger than the guide portion 109. A stem 111 of a movable pressing part 112 extends slidably and sealingly through the guide portion and the passage 110 of the stationary part 106. At a first outer end, the stem is provided with a head 113 having a pressing face 114 facing the pressing face 115 of the stationary part 106, into which the passage 110 opens. At the opposite end of the stem 111 a core 116 of an increased diameter is provided. A compression spring is arranged between the core 116 and the end face 1 17 of the stationary part 106 opposing the pressing face thereof, said spring acting to press the pressing faces of the two parts into engagement with each other. An electric coil 118, a so-called solenoid coil, is arranged about the core 116 of movable part 112. The coil 118 is connected to the wall 108 by means of connecting rods 132. The electric coil 118 is connected to a power supply 120 via a control system 119. The control system 119 and the power supply (battery) 120 are arranged in a compartment 121 closed by means of a sliding lid 122.

A pivoting, small, thin flap or blade 124 is arranged in the interior of the inhalation part 101 between the filter 102 and the coil 118. The flap is provided with a micromagnet intended to act on a reed relay 125 connected to the control system 119, when the thin flap pivots.

The device shown is, furthermore, provided with a compartment 126 intended to slidably receive a small medicine container 127 in the manner described in connection with the embodiment shown in FIG. 1. The small medicine container 127 is of the same type as the one described above with reference to FIG. 1, for which reason the operation thereof is not described in details. The compartment 126 is arranged and formed in such a manner that the discharge tube 128 of the small medicine container extends radially relative to the axis of the stationary pressing part 106. The stationary part 106 is provided with a radial bore 129 extending into the passage 110 and intended to receive the outer end of the discharge tube 128 resting on a ledge in the bore 129.

The device shown in FIG. 5 operates in the following manner:

By pressing the activation button 130 extending through the detachable cover 13 1, the small medicine container (except the discharge tube 128) is moved downwards, whereby fluid from the interior of the container flows out of the discharge tube 128 and into the passage 110. The passage is sealed at its outlet end, the pressing faces of the pressing parts engaging one another due to the force of the spring 123.

Inhalation at the end portion 132 of the inhalation part 10 causes air to flow through the filter 102. The air flow causes the thin flap 124 with the micromagnet to pivot and thereby close the reed relay 125 which in turn activates the control system 119 supplied with power from the power supply 120. As described above, the control system 119 causes alternately positive and negative pulses to be supplied to the coil 118. The pulses causes the core 116 to be moved axially backwards and forwards for alternately bringing the pressing face of the head 113 into and out of engagement with the pressing face 115 of the stationary pressing part. A small amount of fluid flows onto the pressing face 115 of the stationary part and adheres thereto during the opening movement. At the subsequent closing movement, said amount of fluid is radially pressed out as a film breaking into droplets to be entrained by the inhalation air. After a certain amount of time, typically in the order of 2 seconds, the control system discontinues the supply of power to the coil 118 and the discharge of atomised fluid stops, the spring 123 causing the parts to sealingly abut one another.

I claim:

1. A method of atomising fluids, wherein a predetermined quantity of fluid is provided between a first surface and a second surface spaced from one another, whereafter the first and second surfaces are moved towards one another, until the first surface essentially over its entire extent essentially is in contact with the second surface and at such a speed that the fluid between the first and second surfaces is pressed out to the surroundings via the periphery of the surfaces with a velocity sufficient to atomise the fluid wherein the relative motion of the first and second surfaces causes the atomisation of the fluid.

2. A method as claimed in claim 1, wherein the first and second surfaces have essentially complementary shapes.

3. A method as claimed in claim 1, wherein the fluid is supplied through an outlet which opens into one of the surfaces, preferably centrally therein.

4. A method as claimed in claim 1, wherein the first and second surfaces alternately are moved between the position, in which they are spaced from one another and the position, in which they essentially are in contact with one another.

5. A device for carrying out the method according to claim 1, said device comprising a first pressing means having the first surface and a second pressing means having the second surface, said first and second pressing means being arranged with the surfaces facing one another, a drive means for moving one of the pressing means alternately between a position, in which the surfaces of the first and second pressing means are spaced from one another and a position, in which said surfaces essentially engage one another over their entire extent, a fluid outlet opening into an area between the two pressing means, said outlet communicating with a fluid supply and a dosage means through a fluid supply passage, said dosage means supplying a predetermined quantity of fluid to the area between said first and second pressing means through the fluid outlet, when said means are spaced from one another.

6. A device as claimed in claim 5, wherein it comprises a stationary and a movable pressing means.

7. A device as claimed in claim 5, wherein the drive means is an electro-magnetic drive means comprising a displaceable magnetic or electrically conducting core for acting on the movable pressing means and a fixedly arranged coil circumscribing the core, an annular gap being formed therebetween, said coil being supplied intermittently with power from a power supply.

8. A device as claimed in claim 7, wherein the core is fixedly attached to the movable pressing means.

9. A device as claimed in claim 5, wherein one of the surfaces of the first and the second pressing means is slightly concave for the formation of a projecting circumferential edge and formed of a resilient material.

10. A device as claimed in claim 5, wherein stop means are associated with the first and second pressing means for determining a minimum spacing between the first and second surfaces thereof.

* * * * *